(12) United States Patent
Blackburn et al.

(10) Patent No.: US 6,677,343 B2
(45) Date of Patent: Jan. 13, 2004

(54) SUBSTITUTED PIPERAZINE COMPOUNDS

(75) Inventors: Brent K. Blackburn, Los Altos, CA (US); Jeff Zablocki, Mountain View, CA (US); Elfatih Elzein, Fremont, CA (US); Grigory Nudelman, Pacifica, CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 68 days.

(21) Appl. No.: 09/791,262

(22) Filed: Feb. 22, 2001

(65) Prior Publication Data
US 2001/0044541 A1 Nov. 22, 2001

Related U.S. Application Data

(60) Provisional application No. 60/184,206, filed on Feb. 22, 2000.

(51) Int. Cl.$^7$ ............... A61K 31/495; A61K 31/496; C07D 241/04; C07D 405/06; C07D 405/12
(52) U.S. Cl. ............... 514/254.11; 514/255.01; 514/254.09; 544/373; 544/377; 544/391
(58) Field of Search .................. 544/391, 377; 514/255.01, 254.11

(56) References Cited

U.S. PATENT DOCUMENTS

| | | | |
|---|---|---|---|
| 3,710,795 A | | 1/1973 | Higuchi et al. |
| 4,567,264 A | | 1/1986 | Kluge et al. |
| 4,639,452 A | * | 1/1987 | Platel et al. ............... 514/252 |
| 5,472,707 A | | 12/1995 | Samuels et al. |
| 5,506,229 A | | 4/1996 | Dow |
| 5,670,171 A | | 9/1997 | Santus et al. |
| 5,906,988 A | | 5/1999 | Dow |

FOREIGN PATENT DOCUMENTS

| | | | |
|---|---|---|---|
| CA | 2054544 | | 5/1992 |
| DE | 2304155 | * | 8/1974 |
| EP | 0 068 544 | | 1/1983 |
| EP | 0 126 449 | | 11/1984 |
| EP | 0 407 780 | | 1/1991 |
| EP | 0 714 660 | | 6/1996 |
| EP | 0 719 558 | | 7/1996 |
| FR | 2626521 | | 9/1975 |

OTHER PUBLICATIONS

Leuschner, Chemical Abstracts, vol.81, No. 136185 (1974) (Abstract for DE 2304155).*
Fauran et al. Chemical Abstracts, vol.84, No. 121897, Abstract for FR 2262521 (1976).*
Pepine et al., "A Controlled Trial with a Novel Anti-Ischemic Agent, Ranolazine, in Chronic Stable Angina Pectoris That is Responsive to Coventional Antianginal Agents", *American Journal of Cardiology,* vol. 84, pp. 46–50 (1999).
Database WPI, Week 198831, Derwent Publication Ltd., XP–002169972.
Abstract for JP 03141258 Jun. 17, 1991.

\* cited by examiner

*Primary Examiner*—Emily Bernhardt
(74) *Attorney, Agent, or Firm*—McDonnell Boehnen Hulbert & Berghoff

(57) ABSTRACT

Novel compounds of the general formula:

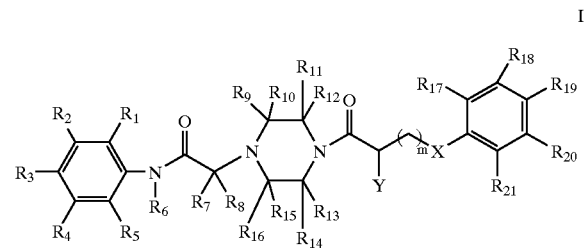

and pharmaceutically acceptable acid addition salts thereof, wherein the compounds are useful in therapy to protect skeletal muscles against damage resulting from trauma or to protect skeletal muscles subsequent to muscle or systemic diseases such as intermittent claudication, to treat shock conditions, to preserve donor tissue and organs used in transplants, in the treatment of cardiovascular diseases including atrial and ventricular arrhythmias, Prinzmetal's (variant) angina, stable angina, and exercise induced angina, congestive heart disease, and myocardial infarction.

25 Claims, No Drawings

SUBSTITUTED PIPERAZINE COMPOUNDS

This application claims priority to U.S. patent application No. 60/184,206 filed on Feb. 22, 2000, the specification of which is incorporated herein by reference.

BACKGROUND OF THE INVENTION

1. Field of the Invention

The present invention is concerned with substituted piperazine compounds, therapeutic dosage forms including one or more of the compounds, and methods for treating diseases in mammals, and in particular, in a human in a therapy selected from the group including protecting skeletal muscles against damage resulting from trauma, protecting skeletal muscles subsequent to muscle or systemic diseases such as intermittent claudication, to treat shock conditions, to preserve donor tissue and organs used in transplants, and to treat cardiovascular diseases including atrial and ventricular arrhythmias, Prinzmetal's (variant) angina, stable angina, and exercise induced angina, congestive heart disease, and myocardial infarction.

2. Description of the Art

U.S. Pat. No. 4,567,264, the specification of which is incorporated herein by reference, discloses a class of substituted piperazine compounds that includes a compound known as ranolazine, (±)-N-(2,6-dimethylphenyl)-4-[2-hydroxy-3-(2-methoxyphenoxy)-propyl]-1-piperazineacetamide, and its pharmaceutically acceptable salts, and their use in the treatment of cardiovascular diseases, including arrhythmias, variant and exercise-induced angina, and myocardial infarction.

U.S. Pat. No. 5,506,229, which is incorporated herein by reference, discloses the use of ranolazine and its pharmaceutically acceptable salts and esters for the treatment of tissues experiencing a physical or chemical insult, including cardioplegia, hypoxic or reperfusion injury to cardiac or skeletal muscle or brain tissue, and for use in transplants. In particular, ranolazine is particularly useful for treating arrhythmias, variant and exercise-induced angina, and myocardial infarction by partially inhibiting cardiac fatty acid oxidation. Conventional oral and parenteral ranolazine formulations are disclosed, including controlled release formulations. In particular, Example 7D of U.S. Pat. No. 5,506,229 describes a controlled release formulation in capsule form comprising microspheres of ranolazine and microcrystalline cellulose coated with release controlling polymers.

Despite the important discovery that ranolazine is a very useful cardiac therapeutic agent, there remains a need for compounds that are partial fatty acid oxidation inhibitors that have a half-life greater than ranolazine and that have activities as least similar to ranolazine.

SUMMARY OF THE INVENTION

This invention includes novel substituted piperazine compounds that are partial fatty acid oxidation inhibitors with good therapeutic half-lives.

This invention also includes novel substituted piperazine compounds that can be administered to a mammal to protect skeletal muscles against damage resulting from trauma, to protecting skeletal muscles subsequent to muscle or systemic diseases such as intermittent claudication, to treat shock conditions, to preserve donor tissue and organs used in transplants, and to treat cardiovascular diseases including atrial and ventricular arrhythmias, Prinzmetal's (variant) angina, stable angina, and exercise induced angina, congestive heart disease, and myocardial infarction.

This invention includes a class of substituted piperazine compounds having the following formula:

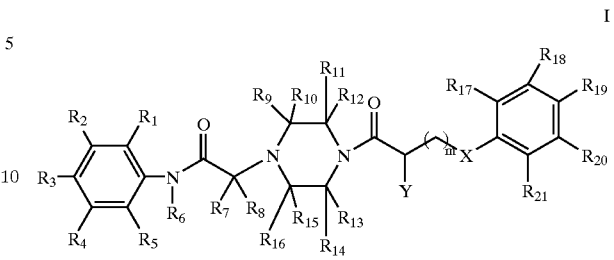

I wherein X=—O— or $(CH_2)_n$; Y=—OH or hydrogen; n=0 or 1; m=0 or 1;

$R_1$, $R_2$, $R_3$, $R_4$ and $R_5$ are each independently selected from the group consisting of hydrogen, halo, $NO_2$, $CF_3$, CN, $OR_{23}$, $SR_{23}$, $N(R_{23})_2$, $S(O)R_{22}$, $SO_2R_{22}$, $SO_2N(R_{23})_2$, $NR_{23}CO_2R_{22}$, $NR_{23}CON(R_{23})_2$, $COR_{23}$, $CO_2R_{23}$, $CON(R_{23})_2$, $NR_{23}SO_2R_{22}$, $C_{1-5}$ alkyl $C_{2-15}$ alkenyl, $C_{2-15}$ alkynyl, heterocyclyl, aryl, and heteroaryl, wherein the alkyl and aryl substituent are optionally substituted with 1 substituent selected from the group consisting of halo, $NO_2$, $CF_3$, CN, $OR_{23}$, $SR_{23}$, $N(R_{23})_2$, $S(O)R_{22}$, and $SO_2R_{22}$;

$R_6$, $R_7$ and $R_8$ each independently selected from the group consisting of hydrogen or $C_{1-15}$ alkyl;

$R_9$, $R_{10}$, $R_{11}$, $R_{12}$, $R_{13}$, $R_{14}$, $R_{15}$, and $R_{16}$ are each independently selected from the group consisting of hydrogen, $CO_2R_{23}$, $CON(R_{23})_2$, $C_{1-4}$ alkyl, or aryl wherein the alkyl and aryl substituents are optionally substituted with 1 substituent selected from the group consisting of halo, $CF_3$, CN, $OR_{23}$, $N(R_{23})_2$, $CO_2R_{23}$, $CON(R_{23})_2$ or aryl, wherein $R_9$ and $R_{10}$ may together form a carbonyl, or $R_{11}$ and $R_{12}$ may together form a carbonyl, or $R_{13}$ and $R_{14}$ may together form a carbonyl, or $R_{15}$ and $R_{16}$ may together form a carbonyl wherein $R_{11}$ and $R_{13}$ or $R_9$ and $R_{15}$ or $R_9$ and $R_{11}$ or $R_{11}$ and $R_{15}$ or $R_9$ and $R_{13}$ may join together to form a bridging ring system wherein the two R groups together comprise of from 1 to 4 carbon atoms and wherein $R_9$ and $R_{10}$ or $R_{11}$ and $R_{12}$ or $R_{13}$ and $R_{14}$ or $R_{15}$ and $R_{16}$ may join to form a bridging ring system wherein the two R groups together comprise of from 1 to 5 carbon atoms;

$R_{17}$, $R_{18}$, $R_{19}$, $R_{20}$, and $R_{21}$, are each independently selected from the group consisting of hydrogen, halo, $NO_2$, $CF_3$, CN, $OR_{23}$, $SR_{23}$, $N(R_{23})_2$, $S(O)R_{22}$, $SO_2R_{22}$, $SO_2N(R_{23})_2$, $NR_{23}CO_2R_{22}$, $NR_{23}CON(R_{23})_2$, $COR_{23}$, $CO_2R_{23}$, $CON(R_{23})_2$, $NR_{23}SO_2R_{22}$, $C_{1-15}$ alkyl, $C_{2-15}$ alkenyl, $C_{2-15}$ alkynyl, heterocyclyl, aryl, and heteroaryl, wherein the alkyl and aryl substituent are optionally substituted with 1 substituent selected from the group consisting of halo, $NO_2$, $CF_3$, CN, $OR_{23}$, $SR_{23}$, $N(R_{23})_2$, $S(O)R_{22}$, and $SO_2R_{22}$;

$R_{22}$ is selected from the group consisting of $C_{1-15}$ alkyl, aryl, or heteroaryl, wherein the alkyl and aryl substituents are optionally substituted with 1 substituent selected from the group consisting of halo, alkyl, monoalkylamino, dialkylamino, alkyl amide, aryl amide, heteroaryl amide, CN, O—$C_{1-6}$ alkyl, $CF_3$, or heteroaryl; and $R_{23}$ is selected from the group consisting of H, $C_{1-15}$ alkyl, aryl, or heteroaryl, wherein the alkyl and aryl substituents are optionally substituted with 1 substituent selected from the group consisting of halo, alkyl, mono- or dialkylamino, alkyl, CN, —O—$C_{1-6}$ alkyl, or $CF_3$.

In another embodiment, this invention is a compound having the formula above wherein X=—O—or $(CH_2)_n$; Y=—OH or hydrogen; n=0 or 1; m=0 or 1;

$R^1$, $R^2$, $R^3$, $R^4$ and $R_5$ are each independently selected from the group consisting of hydrogen, halo, $CF_3$, $OR^{22}$ and $C_{1-4}$ alkyl wherein $R^{22}$ is a member selected from the group consisting of $C_{1-3}$ alkyl;

$R^6$, $R^7$ and $R^8$ each independently selected from the group consisting of hydrogen and $C_{1-3}$ alkyl;

$R^9$, $R^{10}$, $R^{11}$, $R^{12}$, $R^{13}$, $R^{14}$, $R^{15}$ and $R^{16}$ are each independently selected from hydrogen, $C_{1-4}$ alkyl, or $R^9$ and $R^{10}$ may together form a carbonyl, or $R^{15}$ and $R^{16}$ may together form a carbonyl or $R^{10}$ and $R^{11}$ may together form —$CH_2CH_2CH_2CH_2$—; and $R^{17}$, $R^{18}$, $R^{19}$, $R^{20}$ and $R^{21}$ are each independently selected from the group consisting of hydrogen, halo, $CF_3$, CN, $OR^{22}$, $S(O)R^{22}$, $SO_2R^{22}$, $SON(R^{22})_2$, $CON(R^{22})_2$, $C_{1-4}$ alkyl, or $R^{17}$ and $R^{18}$ may together form —CH=CH—CH=CH—, or $R^{18}$ and $R^{19}$ may together form —OCH$_2$O—, wherein $R^{22}$ is $C_{1-3}$ alkyl. In still another embodiment, this invention is a substituted piperazine compound selected from the group consisting of N-(2,6-dimethylphenyl)-2-[4-(2-hydroxy-3-phenylpropanoyl) piperazinyl]acetamide, N-(2,6-dimethylphenyl)-2-[4-(2-hydroxy-3-indol-3-ylpropanoyl)piperazinyl]acetamide, N-(2,6-dimethylphenyl)-2-[4-(2-hydroxy-4-phenylbutanoyl)piperazinyl]acetamide, N-(2,6-dimethylphenyl)-2-{4-[2-(2-chlorophenoxy)acetyl]piperazinyl}acetamide, N-(2,6-dimethylphenyl)-2-[4-(4-phenylbutanoyl)piperazinyl]acetamide, N-(2,6-dimethylphenyl)-2-[4-(3-phenylpropanoyl)piperazinyl] acetamide, N-(2,6-dimethylphenyl)-2-[4-(2-phenylacetyl) piperazinyl]acetamide, N-(2,6-dimethylphenyl)-2-[4-(2-hydroxy-3-indol-3-ylpropanoyl)piperazinyl]acetamide, and 2-[4-((2R)-2-hydroxy-4-phenylbutanoyl)piperazinyl]-N-(2,6-dimethylphenyl)acetamide.

In yet another embodiment, this invention is a method for administering one or more composition of this invention to a mammal in a treatment selected from the group consisting of protecting skeletal muscles against damage resulting from trauma, protecting skeletal muscles subsequent to muscle or systemic diseases such as intermittent claudication, to treat shock conditions, to preserve donor tissue and organs used in transplants, and to treat cardiovascular diseases including atrial and ventricular arrhythmias, Prinzmetal's (variant) angina, stable angina, and exercise induced angina, congestive heart disease, and myocardial infarction.

DETAILED DESCRIPTION OF THE INVENTION

This invention concerns substituted piperazine compounds having the following formula:

I wherein X=—O— or $(CH_2)_n$;
Y=—OH or hydrogen;
n=0 or 1;
m=0 or 1;
$R^1$, $R^2$, $R^3$, $R^4$ and $R^5$ are each independently selected from the group consisting of hydrogen, halo, $CF_3$, $OR^{22}$ and $C_{1-4}$ alkyl wherein $R^{22}$ is a member selected from the group consisting of $C_{1-3}$ alkyl;

$R^6$, $R^7$ and $R^8$ each independently selected from the group consisting of hydrogen and $C_{1-3}$ alkyl;

$R^9$, $R^{10}$, $R^{11}$, $R^{12}$, $R^{13}$, $R^{14}$, $R^{15}$ and $R^{16}$ are each independently selected from hydrogen, $C_{1-4}$ alkyl, or $R^9$ and $R^{10}$ may together form a carbonyl, or $R^{15}$ and $R^{16}$ may together form a carbonyl or $R^{10}$ and $R^{11}$ may together form —$CH_2CH_2CH_2CH_2$—; and $R^{17}$, $R^{18}$, $R^{19}$, $R^{20}$ and $R^{21}$ are each independently selected from the group consisting of hydrogen, halo, $CF_3$, CN, $OR^{22}$, $S(O)R^{22}$, $SO_2R^{22}$, $SON(R^{22})_2$, $CON(R^{22})_2$, $C_{1-4}$ alkyl, or $R^{17}$ and $R^{18}$ may together form —CH=CH—CH=CH—, or $R^{18}$ and $R^{19}$ may together form —OCH$_2$O—, wherein $R^{22}$ is $C_{1-3}$ alkyl.

In preferred compositions, $R^1$, $R^2$, $R^3$, $R^4$ and $R^5$ are each independently selected from the group consisting of hydrogen, $OR^{22}$ and $C_{1-4}$ alkyl wherein $R^{22}$ is a member selected from the group consisting of $C_{1-3}$ alkyl;

$R^6$, $R^7$ and $R^8$ each independently selected from the group consisting of hydrogen and methyl;

$R^9$, $R^{10}$, $R^{11}$, $R^{12}$, $R^{13}$, $R^{14}$, $R^{15}$ and $R^{16}$ are each independently selected from hydrogen, and $C_{1-3}$ alkyl; and $R^{17}$, $R^{18}$, $R^{19}$, $R^{20}$ and $R^{21}$ are each independently selected from the group consisting of hydrogen, halo, $CF_3$, $OR^{22}$, $C_{1-2}$ alkyl, or $R^{18}$ and $R^{19}$ may together form —OCH$_2$O—, wherein $R^{22}$ is $C_{1-2}$ alkyl.

In still more preferred compositions, $R^1$, $R^2$, $R^3$, $R^4$ and $R^5$ are each independently selected from the group consisting of hydrogen, and $C_{1-2}$ alkyl;

$R^6$, $R^7$ and $R^8$ are each hydrogen;

$R^9$, $R^{10}$, $R^{11}$, $R^{12}$, $R^{13}$, $R^{14}$, $R^{15}$ and $R^{16}$ are each independently selected from hydrogen, ethyl and methyl; and $R^{17}$, $R^{18}$, $R^{19}$, $R^{20}$ and $R^{21}$ are each independently selected from the group consisting of hydrogen, halo, $CF_{1-3}$, $OR^{22}$, methyl, wherein $R^{22}$ is methyl.

In yet more preferred compositions, $R^1$ and $R^5$ are each methyl;

$R^2$, $R^3$, $R^4$, $R^6$, $R^7$, $R^8$, $R^9$, $R^{10}$, $R^{11}$, $R^{12}$, $R^{13}$, $R^{14}$, $R^{15}$ and $R^{16}$ are each hydrogen; and $R^{17}$, $R^{18}$, $R^{19}$, $R^{20}$ and $R^{21}$ are each independently selected from the group consisting of hydrogen and halo.

Most preferably, the substituted piperazine compounds of this invention are selected from the group consisting of N-(2,6-dimethylphenyl)-2-[4-(2-hydroxy-3-phenylpropanoyl)piperazinyl]acetamide, N-(2,6-dimethylphenyl)-2-[4-(2-hydroxy-3-indol-3-ylpropanoyl) piperazinyl]acetamide, N-(2,6-dimethylphenyl)-2-[4-(2-hydroxy-4-phenylbutanoyl)piperazinyl]acetamide, N-(2,6-dimethylphenyl)-2-{4-[2-(2-chlorophenoxy)acetyl] piperazinyl}acetamide, N-(2,6-dimethylphenyl)-2-[4-(4-phenylbutanoyl)piperazinyl]acetamide, N-(2,6-dimethylphenyl)-2-[4-(3-phenylpropanoyl)piperazinyl] acetamide, N-(2,6-dimethylphenyl)-2-[4-(2-phenylacetyl) piperazinyl]acetamide, N-(2,6-dimethylphenyl)-2-[4-(2-hydroxy-3-indol-3-ylpropanoyl)piperazinyl]acetamide, and 2-[4-((2R)-2-hydroxy-4-phenylbutanoyl)piperazinyl]-N-(2,6-dimethylphenyl)acetamide.

The following definitions apply to terms as used herein.

"Halo" or "Halogen"—alone or in combination means all halogens, that is, chloro (Cl), fluoro (F), bromo (Br), iodo (I).

"Hydroxyl" refers to the group —OH.

"Thiol" or "mercapto" refers to the group —SH.

"Alkyl"—alone or in combination means an alkane-derived radical containing from 1 to 20, preferably 1 to 15, carbon atoms (unless specifically defined). It is a straight chain alkyl, branched alkyl or cycloalkyl. Preferably, straight or branched alkyl groups containing from 1–15, more preferably 1 to 8, even more preferably 1–6, yet more preferably 1–4 and most preferably 1–2, carbon atoms, such as methyl, ethyl, propyl, isopropyl, butyl, t-butyl and the like. The term "lower alkyl" is used herein to describe the straight chain alkyl groups described immediately above. Preferably, cycloalkyl groups are monocyclic, bicyclic or tricyclic ring systems of 3–8, more preferably 3–6, ring members per ring, such as cyclopropyl, cyclobutyl, cyclopentyl, cyclohexyl, adamantyl and the like. Alkyl also includes a straight chain or branched alkyl group that contains or is interrupted by a cycloalkyl portion. The straight chain or branched alkyl group is attached at any available point to produce a stable compound. Examples of this include, but are not limited to, 4-(isopropyl)-cyclohexylethyl or 2-methyl-cyclopropylpentyl. A substituted alkyl is a straight chain alkyl, branched alkyl, or cycloalkyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Alkenyl"—alone or in combination means a straight, branched, or cyclic hydrocarbon containing 2–20, preferably 2–17, more preferably 2–10, even more preferably 2–8, most preferably 2 to 4 carbon atoms with at least one, preferably 1–3, more preferably 1–2, and most preferably one, carbon to carbon double bond. In the case of a cycloalkyl group, conjugation of more than one carbon to carbon double bond is not such as to confer aromaticity to the ring. Carbon to carbon double bonds may be either contained within a cycloalkyl portion, with the exception of cyclopropyl, or within a straight chain or branched portion. Examples of alkenyl groups include ethenyl, propenyl, isopropenyl, butenyl, cyclohexenyl, cyclohexenylalkyl and the like. A substituted alkenyl is the straight chain alkenyl, branched alkenyl or cycloalkenyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N- mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxy, alkoxycarbonyl, aryloxycarbonyl, heteroaryloxycarbonyl, or the like attached at any available point to produce a stable compound.

"Alkynyl"—alone or in combination means a straight or branched hydrocarbon containing 2–20, preferably 2–17, more preferably 2–10, even more preferably 2–8, most preferably 2–4, carbon atoms containing at least one, preferably one, carbon to carbon triple bond. Examples of alkynyl groups include ethynyl, propynyl, butynyl and the like. A substituted alkynyl refers to the straight chain alkynyl or branched alkynyl defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like attached at any available point to produce a stable compound.

"Alkyl alkenyl" refers to a group —R—CR'=CR'''R'''', where R is lower alkyl, or substituted lower alkyl, R', R''', R'''' may independently be hydrogen, halogen, lower alkyl, substituted lower alkyl, acyl, aryl, substituted aryl, hetaryl, or substituted hetaryl as defined below.

"Alkyl alkynyl" refers to a groups —RC≡CR' where R is lower alkyl or substituted lower alkyl, R' is hydrogen, lower alkyl, substituted lower alkyl, acyl, aryl, substituted aryl, hetaryl, or substituted hetaryl as defined below.

"Alkoxy" denotes the group —OR, where R is lower alkyl, substituted lower alkyl, acyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined.

"Alkylthio" denotes the group —SR, —S(O)$_{n=1-2}$—R, where R is lower alkyl, substituted lower alkyl, aryl, substituted aryl, aralkyl or substituted aralkyl as defined herein.

"Acyl" denotes groups —C(O)R, where R is hydrogen, lower alkyl substituted lower alkyl, aryl, substituted aryl and the like as defined herein.

"Aryloxy" denotes groups —OAr, where Ar is an aryl, substituted aryl, heteroaryl, or substituted heteroaryl group as defined herein.

"Amino" denotes the group NRR!, where R and R' may independently by hydrogen, lower alkyl, substituted lower alkyl, aryl, substituted aryl, hetaryl, or substituted hetaryl as defined herein or acyl.

"Amido" denotes the group —C(O)NRR', where R and R' may independently by hydrogen, lower alkyl, substituted lower alkyl, aryl, substituted aryl, hetaryl, substituted hetaryl as defined herein.

"Carboxyl" denotes the group —C(O)OR, where R is hydrogen, lower alkyl, substituted lower alkyl, aryl, substituted aryl, hetaryl, and substituted hetaryl as defined herein.

"Aryl"—alone or in combination means phenyl or naphthyl optionally carbocyclic fused with a cycloalkyl of preferably 5–7, more preferably 5–6, ring members and/or optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N- mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Substituted aryl" refers to aryl optionally substituted with one or more functional groups, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heterocycle" refers to a saturated, unsaturated, or aromatic carbocyclic group having a single ring (e.g., morpholino, pyridyl or furyl) or multiple condensed rings (e.g., naphthpyridyl, quinoxalyl, quinolinyl, indolizinyl or benzo[b]thienyl) and having at least one hetero atom, such as N, O or S, within the ring, which can optionally be unsubstituted or substituted with, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heteroaryl"—alone or in combination means a monocyclic aromatic ring structure containing 5 or 6 ring atoms, or a bicyclic aromatic group having 8 to 10 atoms, containing one or more, preferably 1–4, more preferably 1–3, even more preferably 1–2, heteroatoms independently selected from the group O, S, and N, and optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di- substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable aromatic ring is retained. Examples of heteroaryl groups are pyridinyl, pyridazinyl, pyrazinyl, quinazolinyl, purinyl, quinolinyl, isoquinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl, benzothiazolyl, benzoxazolyl, and the like. A substituted heteroaryl contains a substituent attached at an available carbon or nitrogen to produce a stable compound.

"Heterocyclyl"—alone or in combination means a non-aromatic cycloalkyl group having from 5 to 10 atoms in which from 1 to 3 carbon atoms in the ring are replaced by heteroatoms of O, S or N, and are optionally benzo fused or fused heteroaryl of 5–6 ring members and/or are optionally substituted as in the case of cycloalkyl. Heterocycyl is also intended to include oxidized S or N, such as sulfinyl, sulfonyl and N-oxide of a tertiary ring nitrogen. The point of attachment is at a carbon or nitrogen atom. Examples of heterocyclyl groups are tetrahydrofuranyl, dihydropyridinyl, piperidinyl, pyrrolidinyl, piperazinyl, dihydrobenzofuryl, dihydroindolyl, and the like. A substituted hetercyclyl contains a substituent nitrogen attached at an available carbon or nitrogen to produce a stable compound.

"Substituted heteroaryl" refers to a heterocycle optionally mono or poly substituted with one or more functional groups, e.g., halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Aralkyl" refers to the group —R—Ar where Ar is an aryl group and R is lower alkyl or substituted lower alkyl group. Aryl groups can optionally be unsubstituted or substituted with, e.g., halogen, lower alkyl, alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Heteroarylalkyl" refers to the group —R—HetAr where HetAr is an heteroaryl group and R lower alkyl or substituted lower alkyl. Heteroarylalkyl groups can optionally be unsubstituted or substituted with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloalkyl" refers to a divalent cyclic or polycyclic alkyl group containing 3 to 15 carbon atoms.

"Substituted cycloalkyl" refers to a cycloalkyl group comprising one or more substituents with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Alkyl cycloalkyl" denotes the group —R—cycloalkyl where cycloalkyl is a cycloalkyl group and R is a lower alkyl or substituted lower alkyl. Cycloalkyl groups can optionally be unsubstituted or substituted with e.g. halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Optional" and "optionally" mean that the subsequently described event or circumstance may or may not occur, and that the description includes instances where the event or circumstance occurs and instances in which it does not. For example, "optional pharmaceutical excipients" indicates that a formulation so described may or may not include pharmaceutical excipients other than those specifically stated to be present, and that the formulation so described includes instances in which the optional excipients are present and instances in which they are not.

"Treating" and "treatment" refer to any treatment of a disease in a mammal, particularly a human, and include:

(i) preventing the disease from occurring in a subject which may be predisposed to the disease but has not yet been diagnosed as having it;

(ii) inhibiting the disease, i.e., arresting its development; or (iii) relieving the disease, i.e., causing regression of the disease.

The compositions of this invention are useful for treating mammals in a therapy selected from the group consisting of protecting skeletal muscles against damage resulting from trauma, protecting skeletal muscles subsequent to muscle or systemic diseases such as intermittent claudication, to treat shock conditions, to preserve donor tissue and organs used in transplants, and to treat cardiovascular diseases including atrial and ventricular arrhythmias, Prinzmetal's (variant) angina, stable angina, and exercise induced angina, congestive heart disease, and myocardial infarction. The treatment is accomplished using a therapeutically effective amount of at least one compound of this invention and/or a pharmaceutically acceptable acid addition salt thereof in admixture with a pharmaceutically acceptable excipient.

Compounds falling within the scope of this invention include the optical isomers (+) and (−) and R- and S- isomers of the above-identified compounds and mixtures thereof. This invention includes the individual isomers and all possible mixtures thereof.

All of the aforementioned embodiments include the pharmaceutically acceptable acid addition salts thereof, particularly the mono- and dihydrochlorides, and mixtures thereof.

The compounds having the general formula I can be prepared as outlined in Schemes 1–5. A general synthesis of the compounds of this invention is outlined in Scheme 1. Compound IV can be prepared by N-acylation of substituted aniline II with 2-substituted chloroacetylchloride III. Compound II is available commercially or readily prepared through reduction of the corresponding nitrobenzene derivative (acid/SnCl$_2$ or catalytic hydrogenation, see Advanced Organic Chemistry, Ed. J. March, (1992) A. Wiley-Interscience). Some examples of commercially available substituted aniline II include 2,6-dimethylaniline, 2,3-dimethylaniline, 2-methylaniline 4-methylaniline, 4-methylaniline, 2,4-dichloroaniline, 3,4-dichloroaniline, 2,5-dichloroaniline, 2,4-dichloroaniline, 2-chloroaniline, 3-chloroaniline, 2,6-difluoroaniline, 2,5-difluoroaniline, 3,4-difluoroaniline, 2-fluoroaniline, 4-fluoroaniline, 3-fluoroaniline, 2-fluoro-6-chloroaniline, 4-fluoro-3-chloroaniline.

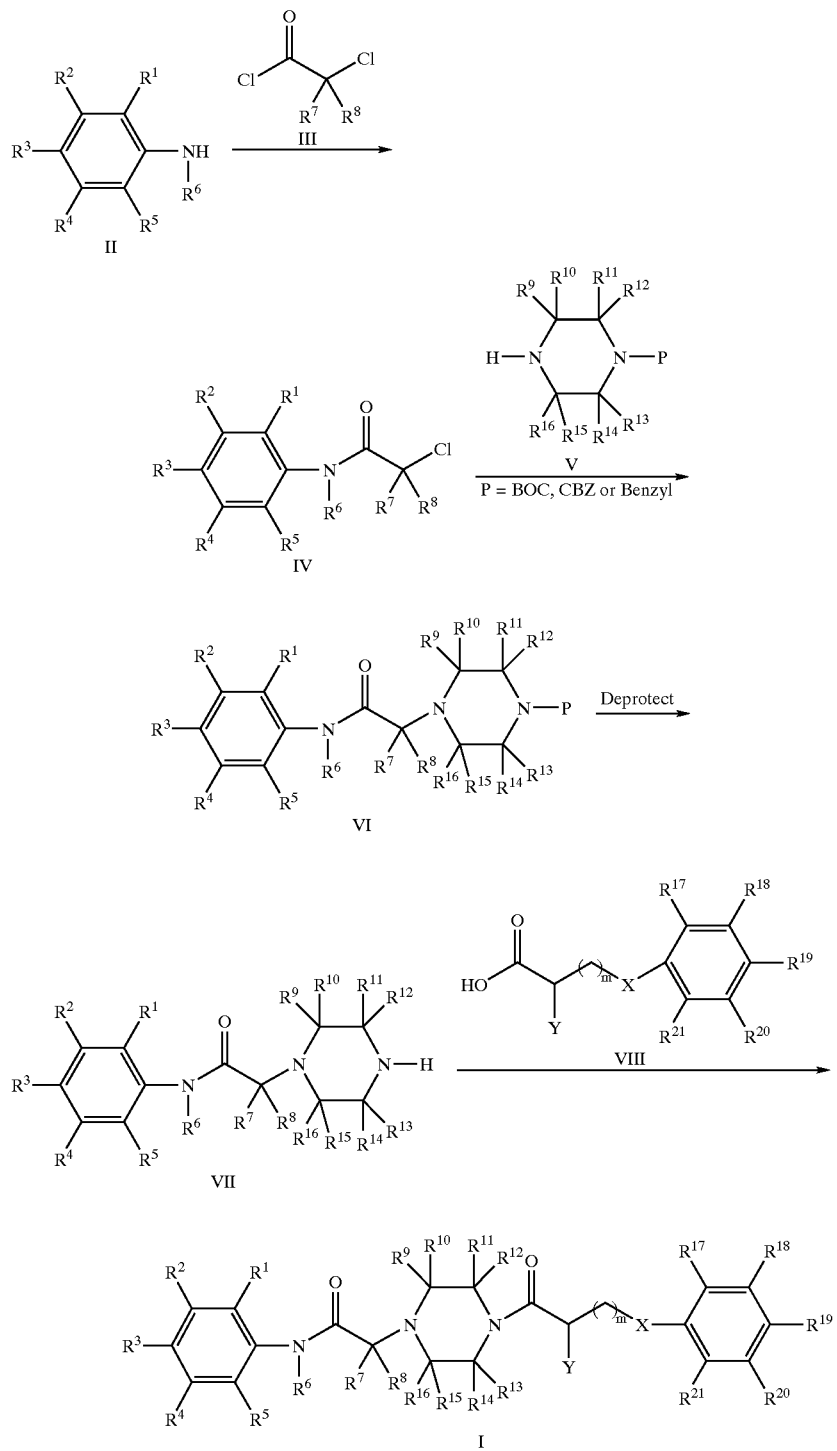

Compound VI can be obtained by reacting compound IV with N-protected substituted piperazine V through warming in an appropriate solvent (e.g. DMF, EtOH). Protection of the nitrogen of compound V is only required when it is useful to control the regiochemistry of the addition of Compound V with compound IV. In some cases, compound V can be obtained from commercial sources. Examples of commercially available compounds of general structure V include 2-methyl piperazine, 2,5-dimethyl piperazine, 2,6-dimethyl piperazine and 4-benzyloxycarbonylpiperazin-2-one. Deprotection of compound VI can be accomplished using the standard conditions (e.g. for Boc group use TFA, for CBZ and benzyl use hydrogenation). Compound I can be prepared by coupling compound VII with carboxylic acid VIII (eg. EDC or HBTU). Compound VIII can be obtained from commercial sources. Examples of commercially available compounds corresponding to general structure VIII include -phenyllactic acid, 3-Indollactic acid, R-2-hydroxy-4-phenylbutyric acid, hydrocinnamic acid, 3-(2-methoxyphenyl)propionic acid, 3-(2,3,4-trimethoxyphenyl)propionic acid, 3-(2,3,-dimethoxyphenyl)propionic acid, and 4-phenylbutyric acid.

Compound I can alternatively be prepared as described in scheme 2. Compound X can be obtained through N-acylation of VII with chloroacetic anhydride.

Heating substituted phenol XI with compound X with potassium carbonate in acetone yield compound I wherein Y=H, M=0, X=O. Examples of commercially available substituted phenols include 2-cholorophenol, 2-fluorophenol, 2-methoxyphenol, 2-methylphenol sesamol, 2,6-dichlorophenol, 3,5-dichlorophenol, 2,6-difluorophenol, 2,4-difluorophenol, 5-indanol, 3-chloro-4-fluorophenol, 2-chloro-4-fluorophenol and 5,6,7,8-tetrahydro-2-naphthol.

Compound V can be prepared as described in Scheme 3. Alkylation of compound XII with alkyl halides using t-BuLi as base can afford compound XIII as described by Pohlman et. al. (J. Org. Chem, (1997), 62, 1016–1022). Reduction of XV using diborane can afford N-benzyl protected version of compound V after N-Boc deprotection with trifluoroacetic acid (TFA, for the diborane reduction see Jacobson et. al, J. Med. Chem, (1999), 42, 1123–1144).

SCHEME 3

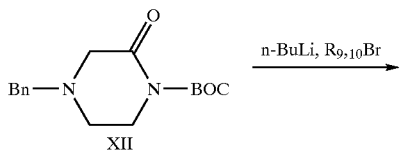

XII

SCHEME 2

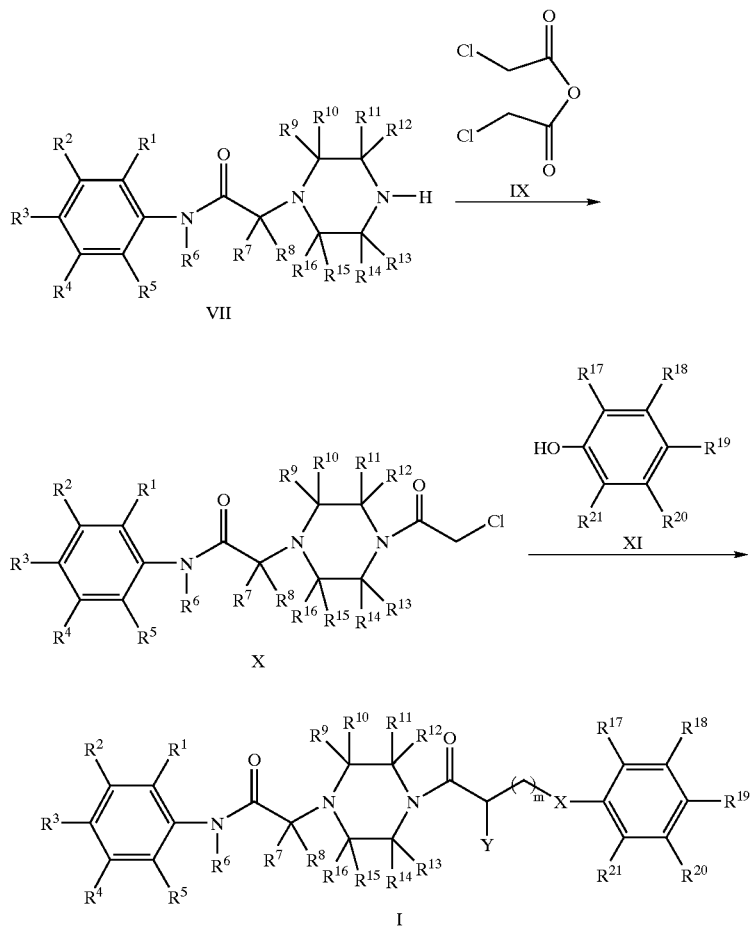

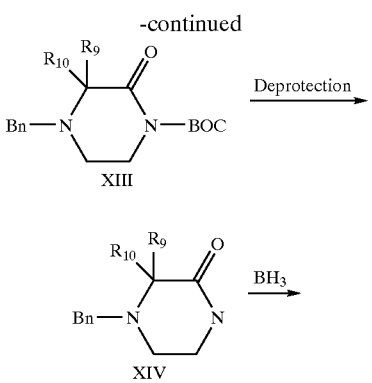

Compound V can also be prepared through standard coupling (eg. EDC or PyBroP) and deprotection of D or L amino acids as outlined in Scheme 4 [For preparations of diketopiperazines see—P. Cledera et al. Tetrahedron, (1998) p. 12349–12360 and R. A. Smith et al Bioorg. Med. Chem. Lett. (1998) p. 2369–2374]. Reduction of the diketopiperazine with diborane can afford the N-benzyl protected version of compound V.

SCHEME 4

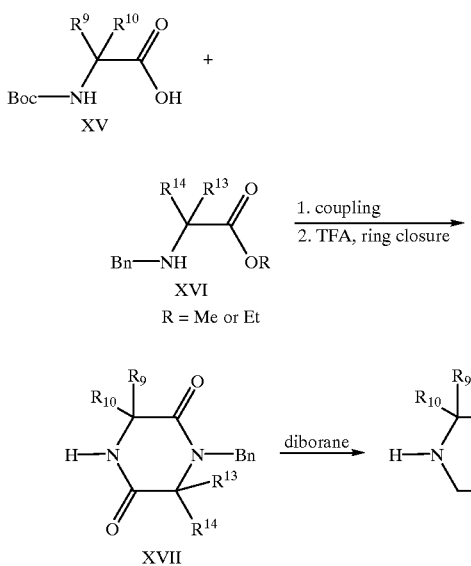

A specific example of the preparation of a compound from this invention is disclosed in Scheme 5 to further illustrate how to prepare the compounds of this invention. In particular, 2,6-dichloroaniline 1 was acylated with 2-chloroacetyl chloride 2 using saturated bicarbonate and ether (1:1) as base and co-solvent, respectively to afford the chloroacetamide derivative 3. Further reaction of compound 3 with piperazine afforded compound 5 through warming in ethanol. Coupling of compound 5 with (R)-2-hydroxy-phenylbutyric acid using standard amino acid coupling conditions (HBTU, DIPEA,DMAP and THF) yields compound 7.

SCHEME 5

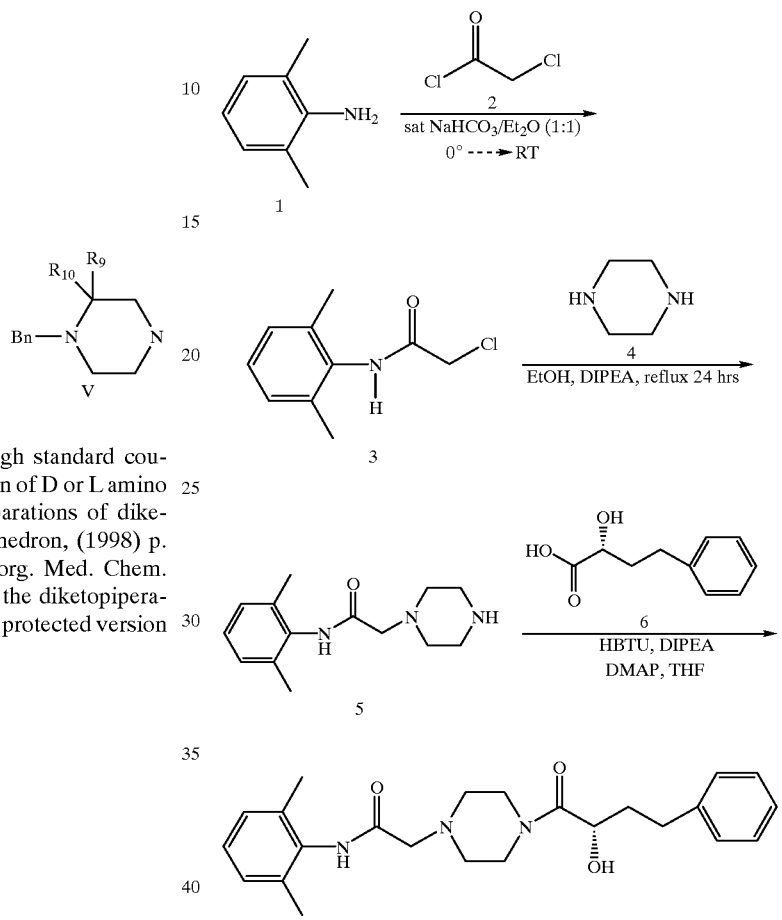

A second example of the preparation of a compound from this invention is disclosed in Scheme 6 to further illustrate how to prepare the compounds of this invention. In particular, previously synthesized 5 was acylated with chloroacetic anhydride 8 to yield the substituted piperazine derivative 9. Compound 11 is prepared by heating compound 9 with 2-chlorophenol in ethanol with potassium carbonate.

SCHEME 6

-continued

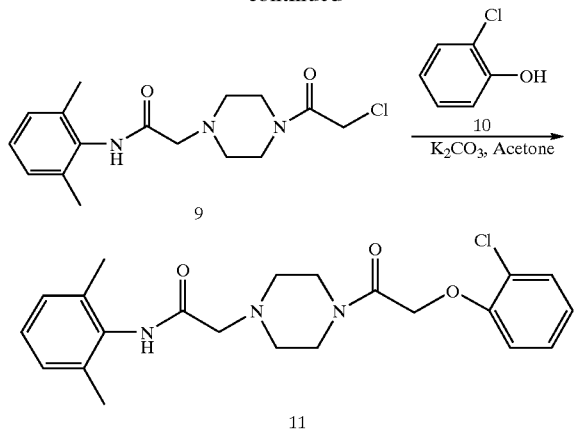

The acid addition salts of the compounds of this invention may be converted to the corresponding free base by treating with a suitable base, such as potassium carbonate or sodium hydroxide, typically in the presence of aqueous solvent, and at a temperature of between about 0 degrees C. and 100 degrees C. The free base form is isolated by conventional means, such as extraction with an organic solvent.

Salts of the compounds of this invention may be interchanged by taking advantage of differential solubilities and volatilities, or by treating with the appropriately loaded ion exchange resin. This conversion is carried out at a temperature between about 0° C. and the boiling point of the solvent being used as the medium for the procedure. Administration of the active compounds and salts described herein can be via any of the accepted modes of administration for therapeutic agents. These methods include oral, parenteral, transdermal, subcutaneous and other systemic modes. The preferred method of administration is oral, except in those cases where the subject is unable to ingest, by himself, any medication. In those instances it may be necessary to administer the composition parentarally.

Depending on the intended mode, the compositions may be in the form of solid, semi-solid or liquid dosage forms, such as, for example, tablets, suppositories, pills, capsules, powders, liquids, suspensions, or the like, preferably in unit dosage forms suitable for single administration of precise dosages. The compositions may include one or more conventional pharmaceutical excipients and at least one active compound of this invention or the pharmaceutically acceptable salts thereof and, in addition, may include other medicinal agents, pharmaceutical agents, carriers, adjuvants, diluents, etc.

The amount of active compound administered will, of course, be dependent on the subject being treated, the subject's weight, the severity of the affliction, the manner of administration and the judgment of the prescribing physician. However, an effective dosage is in the range of 0.1–30 mg/kg/day, preferably 0.5–20 mg/kg/day. For an average 70 kg human, this would amount to 7–2100 mg per day, or preferably 35–1400 mg/day. Since many of the effects of the compounds herein (protect skeletal muscles against damage resulting from trauma; protect skeletal muscles subsequent to muscle or systemic diseases such as intermittent claudication; treat shock conditions; preserve donor tissue and organs used in transplants; and treat cardiovascular diseases including atrial and ventricular arrhythmias, Prinzmetal's (variant) angina, stable angina, exercise induced angina, congestive heart disease, and myocardial infarction) are achieved through a similar mechanism (partial fatty acid oxidation inhibition) dosages (and forms of administration) are all generally within the same general and preferred ranges for all these utilities.

For solid compositions, conventional non-toxic solid include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administrable compositions can, for example, be prepared by dissolving, dispersing, etc. an active compound as defined above and optional pharmaceutical adjuvants in a excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound(s), a therapeutically effective amount, i.e. in an amount effective to alleviate the symptoms of the subject being treated. For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 10%–95% active ingredient, preferably 1–70%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795, which is incorporated herein by reference. In another recent approach, the compositions of this invention can be administered orally in a sustained release dosage form using the compositions and/or methods disclosed in U.S. patent application Ser. No. 09/321,522, filed on May 27, 1999, the specification of which is incorporated herein by reference.

It is within the scope of this invention to administer one or more compounds of this invention to a mammal, and preferably to a human by other known routes of pharmaceutical dosage form administration including, but not limited to by bolus, intravenously, transdermally, through The following Examples are representative of the invention, but are not to be construed as limiting the scope of the claims.

Example 1

N-(2,6-dimethylphenyl)-2-[4-(2-hydroxy-4-phenylbutanoyl)piperazinyl]acetamide

Part A: Synthesis of N-(2,6-dimethylphenyl)-2-chloroacetamide (3).

2,6-dimethylaniline (9.8 g, 81.2 mmol) was dissolved in ether (100 mL) and saturated aqueous NaHCO$_3$ (100 mL) and the reaction mixture was cooled in an ice/water bath. To the cold solution was added chloroacetyl chloride 2 (9.17 g, 81.2 mmol) dropwise over a period of 2 h. The mixture was allowed to warm to RT over 14 h. The mixture was diluted with 100 mL ether and the organic layer was dried over MgSO$_4$, filtered and concentrated to afford compound 3 as a white solid.

Part B.

Synthesis of N-(2,6-dimethylphenyl)-2-piperazinylacetamide (5).

To a solution of compound 3 in 100 mL EtOH (5 g, 25.2 mmol) was added compound 4 (2.1 g, 25.0 mmol) and N,N-diisopropylethylamine (3.2 g, 25.2 mmol). The reaction mixture was refluxed for 24 h. The mixture was concentrated in vacuo and the residue was purified by column chromatography (10:1, DCM:MeOH) to afford compound 5.

Part C.

Synthesis of N-(2,6-dimethylphenyl)-2-[4-(2-hydroxy-4phenylbutanoyl) piperazinyl]acetamide (7)

To a solution of 5 in 10ml DMF (0.263g, 1.07mmol) was added compound 6 (0.25g, 1.39mmol), HBTU (0.526g, 1.4mmol), triethylamine (0.108g, 1.07mmol) and DMAP (0.030g, 0.25mmol). The solution was allowed to stir at room temperature for 48h. The solution was concentrated in vacuo. The residue was taken into EtOAc (100ml) and washed with saturated sodium bicarbonate (3×50ml). The organic layer was dried over sodium sulfate and concentrated in vacuo. The residue was purified using prep. TLC (10:1 DCM/MeOH) to afford compound 7: Mass spectrum (M+1)=410.44.

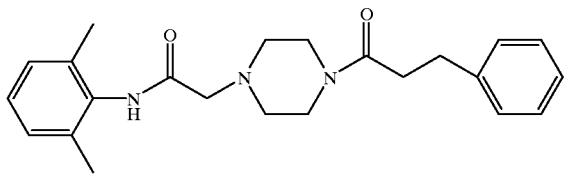

N-(2,6-dimethylphenyl)-2-[4-(3-phenylpropanoyl)piperazinyl]acetamide (12)

Compound 12 was prepared in the manner of compound 7 substituting 3-phenylpropanoic acid for (R)-2-hydroxy-phenylbutyric acid in part C to afford compound 12: Mass spectrum (M+1)=380.40.

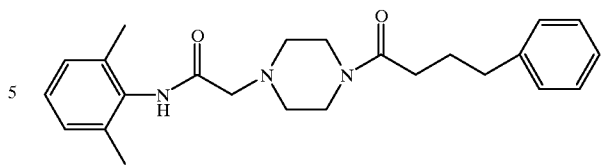

N-(2,6-dimethylphenyl)-2-[4-(4-phenylbutanoyl)piperazinyl]acetamide (13)

Compound 13 was prepared in the manner of compound 7 substituting 4-phenylbutanoic acid for (R)-2-hydroxy-phenylbutyric acid in part C to afford compound 13: Mass spectrum (M+1) =394.40.

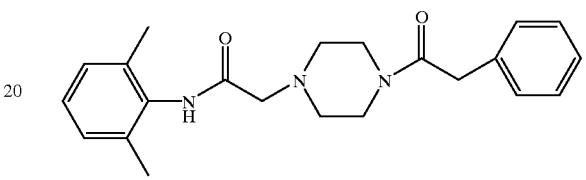

N-(2,6-dimethylphenyl)-2-[4-(2-phenylacetyl)piperazinyl]acetamide (14)

Compound 14 was prepared in the manner of compound 7 substituting 2-phenylacetic acid for (R)-2-hydroxy-phenylbutyric acid in part C to afford compound 14: Mass spectrum (M+1)=366.40.

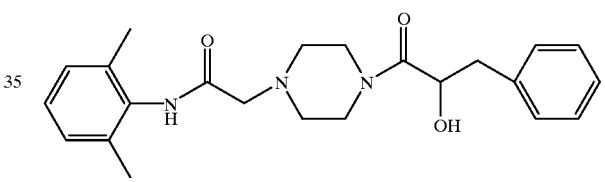

N-(2,6-dimethylphenyl)-2-[4-(2-hydroxy-3-phenylpropanoyl)piperazinyl]acetamide

(15) Compound 15 was prepared in the manner of compound 7 substituting 2-hydroxy-3-phenylpropanoic acid for (R)-2-hydroxy-phenylbutyric acid in part C to afford compound 15: Mass spectrum (M+1)=396.35.

Example 2

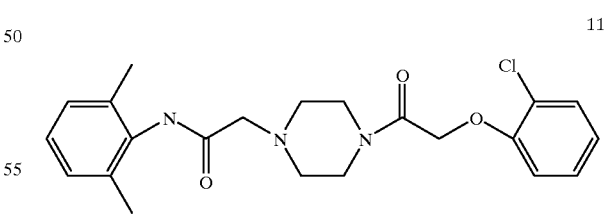

N-(2,6-dimethylphenyl)-2-{4-[2-(2-chlorophenoxy)acetyl]piperazinyl}acetamide (11)

Part A.

Synthesis of N-(2,6-dimethylphenyl)-2-chloroacetamide (3).

2,6-dimethylaniline (9.8 g, 81.2 mmol) was dissolved in ether (100 mL) and saturated aqueous NaHCO$_3$ (100 mL) and the reaction mixture was cooled in an ice/water bath. To the cold solution was added chloroacetyl chloride 2 (9.17 g, 81.2 mmol) dropwise over a period of 2 h. The mixture was allowed to warm to RT over 14 h. The mixture was diluted with 100 mL ether and the organic layer was dried over MgSO$_4$, filtered and concentrated to afford compound 3 as a white solid.

Part B.

Synthesis of N-(2,6-dimethylphenyl)-2-piperazinylacetamide (5).

To a solution of compound 3 in 100 mL EtOH (5 g, 25.2 mmol) was added compound 4 (2.1 g, 25.0 mmol) and N,N-diisopropylethylamine (3.2 g, 25.2 mmol). The reaction mixture was refluxed for 24 h. The mixture was concentrated in vacuo and the residue was purified by column chromatography (10:1, DCM:MeOH) to afford compound 5..

Part C.

Synthesis of N-(2,6-dimethylphenyl)-2-[4-(2-chloroacetyl)piperazinyl]acetamide (9)

To a solution of 5 (1g, 4mmol) in 15ml THF was added chloroacetic anhydride (0.692g, 4mmol). The solution was heated to reflux for one hour. The solvent was evaporated in vacuo and the residue was purified using flash chromatography to yield compound 9.

Part D.

Synthesis of N-(2,6-dimethylphenyl)-2-{4-[2-(2 chlorophenoxy)acetyl]piperazinyl}acetamide (11)

To a solution of 9 (0.194g, 0.6mmol) in 4ml acetone was added 2-chlorophenol (0.092g, 0.72mmol) and potassium carbonate (0.3g, 2.2mmol). The solution was heated to reflux and stirred for 48h. The solution was filtered to remove potassium carbonate, concentrated en vacuo, and purified by Prep TLC (10:1 DCM:MeOH) to yield compound 11. Mass spectrum (M+1)=416.32

2-{4-[2-(2,6-dichlorophenoxy)acetyl]piperazinyl}-N-(2,6-dimethylphenyl)acetamide (16)

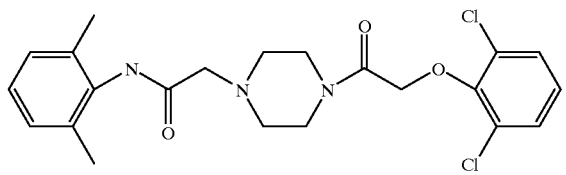

Compound 16 was prepared in a similar manner to 11 substituting 2,6-dichlorophenol with 2-chlorophenol in part D to afford compound 16. Mass spectrum (M+1)=451.23

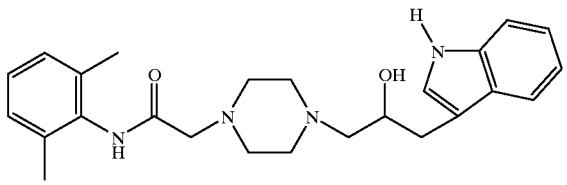

N-(2,6-dimethylphenyl)-2-[4-(2-hydroxy-3-indol-3-ylporpanoyl)piperazinyl]acetamide (17)

Compound 17 was prepared in the manner of compound 7 substituting indole-3-lactic acid for (R)-2-hydroxy-phenylbutyric acid in part C to afford compound 17. Mass spectrum (M+1)=435.46.

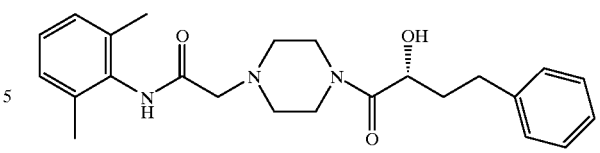

2-[4-((2R)-2-hydroxy-4-phenylbutanoyl)piperazinyl]-N-(2,6-dimethylphenyl)acetamide (18)

Compound 18 was prepared in the manner of compound 7 substituting R-2-hydroxy-4-phenylbutyric acid for (R)-2-hydroxy-phenylbutyric acid in part C to afford compound 18. Mass spectrum (M+1)=410.44.

Example 3

Mitochondrial Assays

Rat heart mitochondria were isolated by the method of Nedergard and Cannon (Methods in Enzymol. 55, 3, 1979). Palmitoyl CoA oxidation—The Palmitoyl CoA oxidation was carried out in a total volume of 100 microliters containing the following agents: 110 mM KCl, 33 mM Tris buffer at pH 8, 2 mM KPi, 2 mM MgCl$_2$, 0.1 mM EDTA, 14.7 microM defatted BSA, 0.5 mM malic acid, 13 mM carnitine, 1 mM ADP, 52 micrograms of mitochondrial protein, and 16 microM 1-C 14 palmitoyl CoA (Sp. Activity 60 mCi/mmole; 20 microCi/ml, using 5 microliters per assay). The compounds of this invention were added in a DMSO solution at the following concentrations: 100 microM, 30 microM, and 3 microM. In each assay, a DMSO control was used. After 15 min at 30 oC, the enzymatic reaction was centrifuged (20,000 g for 1 min), and 70 microliters of the supernatant was added to an activated reverse phase silicic acid column (approximately 0.5 ml of silicic acid). The column was eluted with 2 ml of water, and 0.5 ml of the eluent was used for scintillation counting to determine the amount of $C^{14}$ trapped as $C^{14}$ bicarbonate ion. The data are presented as % activity of control.

TABLE 1

Inhibition of mitochondrial fatty acid oxidation using palmitoyl CoA as substrate - % of Control at 3 concentrations.

| Compound # | 100 µM | 30 µM | 3 µM |
|---|---|---|---|
| Ranolazine | 75% | 90% | — |
| 15 | 64% | — | — |
| 16 | 65% | — | — |
| 7 | 78% | — | — |
| 11 | 80% | — | — |
| 13 | 82% | — | — |
| 12 | 78% | 96% | 103% |
| 17 | 76% | | |
| 18 | 78% | | |
| 14 | 94% | 104% | 107% |

Example 4

Palmitoyl Carnitine Oxidation—The Palmitoyl carnitine oxidation was carried out in a total volume of 100 microliters containing the following agents: 110 mM KCl, 33 mM Tris buffer at pH 8, 2 mM KPi, 2 mM MgCl$_2$, 0.1 mM EDTA, 0.1 mg/ml of defatted BSA, 0.5 mM malic acid, 3 mM ADP, 52 micrograms of mitochondrial protein, and 43 microM 1-C14 palmitoyl carnitine (Sp. Activity 60 mCi/mmole; 20 microCi/ml, using 5 microliters per assay). The compounds of this invention were added in a DMSO solution at the following concentrations: 100 microM, 30 microM, and 3 microM. In each assay, a DMSO control was used. After 15 min at 30° C., the enzymatic reaction was centrifuged (20,000 g for 1 min), and 70 microliters of the supernatant was added to an activated reverse phase silicic acid column (approximately 0.5 ml of silicic acid). The column was eluted with 2 ml of water, and 0.5 ml of the eluent was used for scintillation counting to determine the amount of $C^{14}$ trapped as $C^{14}$ bicarbonate ion. The data are presented as % activity of control.

TABLE 2

Inhibition of mitochondrial fatty acid oxidation using palmitoyl carnitine as substrate - % of Control at 3 concentrations.

| Compound # | 100 μM | 30 μM | 3 μM |
|---|---|---|---|
| Ranolazine | 63% | 98% | — |
| 15 | — | — | — |
| 16 | — | — | — |
| 7 | — | — | — |
| 11 | — | — | — |
| 13 | — | — | — |
| 12 | 79% | 98% | 103% |
| 14 | 88 | 100 | 103 |

We claim:
1. A substituted piperazine compound having the following formula:

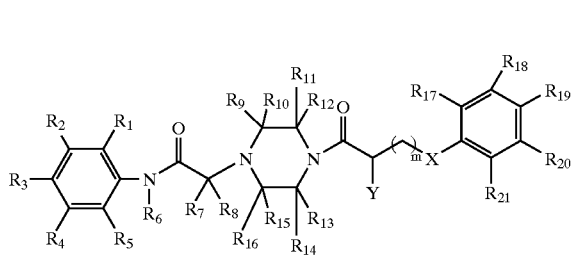

I wherein X=—O— or $(CH_2)_n$;
n=0 or 1;
m=0 or 1;
Y=OH or hydrogen;
$R_1$, $R_2$, $R_3$, $R_4$ and $R_5$ are each independently selected from the group consisting of hydrogen, halo, $CF_3$, and straight or branched $C_{1-4}$ alkyl wherein at least one substituent selected from $R_1$, $R_2$, $R_3$, $R_4$, and $R_5$ cannot be hydrogen;
$R_6$, $R_7$ and $R_8$ each independently selected from the group consisting of hydrogen and straight or branched $C_{1-3}$ alkyl;
$R_9$, $R_{10}$, $R_{11}$, $R_{12}$, $R_{13}$, $R_{14}$, $R_{15}$ and $R_{16}$ are each independently selected from hydrogen or straight or branched $C_{1-4}$ alkyl, or $R_9$ and $R_{10}$ may together form a carbonyl, or $R_{11}$ and $R_{12}$ may together form a carbonyl, or $R_{13}$ and $R_{14}$ may together form a carbonyl, or $R_{15}$ and $R_{16}$ may together form a carbonyl;
$R_{17}$, $R_{18}$, $R_{19}$, $R_{20}$ and $R_{21}$ are each independently selected from the group consisting of hydrogen, halo, $CF_3$, CN, , $S(O)R_{22}$, $SO_2R_{22}$, $SON(R_{22})_2$, $CON(R_{22})_2$, and straight or branched $C_{1-4}$ alkyl, or $R_{17}$ and $R_{18}$ may together form —CH=CH—CH=CH—, or $R_{18}$ and $R_{19}$ may together form —OCH$_2$O—; and
$R_{22}$ is straight or branched $C_{1-3}$ alky,
with the proviso that, when X is $(CH_2)$, then m and n are either both 0 or both 1.
2. The compound of claim 1 wherein m is 0 and n is 0.

3. The compound of claim 1 wherein m is 1 and n is 1.
4. The compound of claim 1 wherein $R_1$, $R_2$, $R_3$, $R_4$ and $R_5$ are each independently selected from the group consisting of hydrogen, and straight or branched $C_{1-4}$ alkyl.
5. The compound of claim 1 wherein $R_6$, $R_7$ and $R_8$ each independently selected from the group consisting of hydrogen and methyl.
6. The compound of claim 1 wherein $R_9$, $R_{10}$, $R_{11}$, $R_{12}$, $R_{13}$, $R_{14}$, $R_{15}$ and $R_{16}$ are each independently selected from hydrogen, or straight or branched $C_{1-3}$ alkyl.
7. The compound of claim 1 wherein $R_{17}$, $R_{18}$, $R_{19}$, $R_{20}$ and $R_{21}$ are each independently selected from the group consisting of hydrogen, halo, $CF_3$, and $C_{1-2}$ alkyl, or $R_{18}$ and $R_{19}$ may together form —OCH$_2$O—.
8. The compound of claim 1 wherein X is $(CH_2)_n$; $R_1$, $R_2$, $R_3$, $R_4$ and $R_5$ are each independently selected from the group consisting of hydrogen, and $C_{1-2}$ alkyl;
$R_6$, $R_7$ and $R_8$ are each hydrogen;
$R_9$, $R_{10}$, $R_{11}$, $R_{12}$, $R_{13}$, $R_{14}$, $R_{15}$ and $R_{16}$ are each independently selected from hydrogen, ethyl, and methyl; and
$R_{17}$, $R_{18}$, $R_{19}$, $R_{20,}$ and $R_{21}$ are each independently selected from the group consisting of hydrogen, halo, $CF_3$, and, methyl.
9. The compound of claim 8 wherein $R_1$ and $R_5$ are each methyl.
10. The compound of claim 8 wherein $R_2$, $R_3$, $R_4$, $R_6$, $R_7$, $R_8$, $R_9$, $R_{10}$, $R_{11}$, $R_{12}$, $R_{13}$, $R_{14}$, $R_{15}$ and $R_{16}$ are each hydrogen.
11. The compound of claim 8 wherein $R_{17}$, $R_{18}$, $R_{19}$, $R_{20}$ and $R_{21}$ are each independently selected from the group consisting of hydrogen and halo.
12. A substituted piperazine compound selected from the group consisting of:
N-(2,6-dimethylphenyl)-2-[4-(2-hydroxy-4-phenylbutanoyl)-piperazinyl]acetamide,
N-(2,6-dimethylphenyl)-2-{4-[2-(2-chlorophenoxy)acetyl]-piperazinyl}acetamide,
N-(2,6-dimethylphenyl)-2-[4-(4phenylbutanoyl)piperazinyl]-acetamide,
N-(2,6-dimethylphenyl)-2-[4-(2-phenylacetyl)piperazinyl]acetamide,
N-(2,6-dimethyl-phenyl)-2-{4-2-[(2,6-dichlorophenoxy)acetyl]-piperazinyl}acetamide, and
2-[4-((2R)-2-hydroxy-4-phenylbutanoyl)piperazinyl]-N-(2,6-dimethylphenyl)acetamide.
13. A substituted piperazine compound having the following formula:

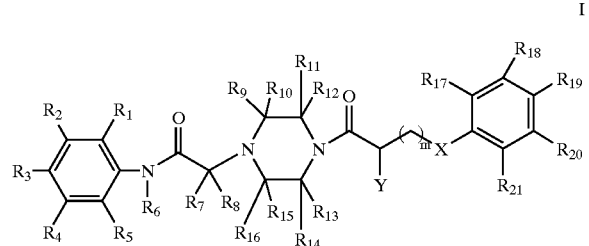

I wherein X=—O—;
Y=OH or hydrogen;
m=0 or 1;
$R_1$, $R_2$, $R_3$, $R_4$ and $R_5$ are each independently selected from the group consisting of hydrogen, halo, $CF_3$, $OR_{22}$ and straight or branched $C_{1-4}$ alkyl;

$R_6$, $R_7$ and $R_8$ each independently selected from the group consisting of hydrogen and straight or branched $C_{1-3}$ alkyl;

$R_9$, $R_{10}$, $R_{11}$, $R_{12}$, $R_{13}$, $R_{14}$, $R_{15}$ and $R_{16}$ are each independently selected from hydrogen, straight or branched $C_{1-4}$ alkyl, or $R_9$ and $R_{10}$ may together form a carbonyl, or $R_{15}$ and $R_{16}$ may together form a carbonyl;

$R_{17}$, $R_{18}$, $R_{19}$, $R_{20}$ and $R_{21}$ are each independently selected from the group consisting of hydrogen, halo, $CF_3$, CN, $OR_{22}$, $S(O)R_{22}$, $SO_2R_{22}$, $SON(R_{22})_2$, $CON(R_{22})_2$, straight or branched $C_{1-4}$ alkyl, or $R_{17}$ and $R_{18}$ may together form —CH=CH—CH=CH—, or $R_{18}$ and $R_{19}$ may together form —OCH$_2$O—; and $R_{22}$ is straight or branched $C_{1-3}$ alkyl.

14. A pharmaceutical composition of matter comprising the compound of claim 1 and one or more pharmaceutical excipients.

15. The pharmaceutical composition of matter of claim 14 wherein the pharmaceutical composition is in the form of a solution.

16. The pharmaceutical composition of matter of claim 14 wherein the pharmaceutical composition is in a form selected from the group consisting of a tablet or a capsule.

17. A method of treating a disease state in a mammal selected from the group consisting of protecting skeletal muscles against damage resulting from trauma, protecting skeletal muscles subsequent to muscle or systemic diseases, shock conditions, preserving donor tissue and organs used in transplants, and cardiovascular diseases, the method comprising administering to a mammal in need thereof, a therapeutically effective amount of a substituted piperazine compound having the following formula:

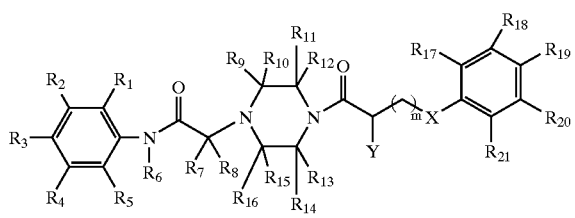

I wherein X=—O— or $(CH_2)_n$;
Y=—OH or hydrogen;
n=0 or 1;
m=0 or 1;
$R_1$, $R_2$, $R_3$, $R_4$ and $R_5$ are each independently selected from the group consisting of hydrogen, halo, $CF_3$, and straight or branched $C_{1-4}$ alkyl, wherein at least one substituent from $R_1$, $R_2$, $R_3$, $R_4$, and $R_5$ cannot be hydrogen;

$R_6$, $R_7$ and $R_8$ each independently selected from the group consisting of hydrogen and straight or branched $C_{1-3}$ alkyl;

$R_9$, $R_{10}$, $R_{11}$, $R_{12}$, $R_{13}$, $R_{14}$, $R_{15}$ and $R_{16}$ are each independently selected from the group consisting of hydrogen, , and straight or branched $C_{1-4}$ alkyl, or $R_9$ and $R_{10}$ may together form a carbonyl, or $R_{11}$ and $R_{12}$ may together form a carbonyl, or $R_{13}$ and $R_{14}$ may together form a carbonyl, or $R_{15}$ and $R_{16}$ may together form a carbonyl;

$R_{17}$, $R_{18}$, $R_{19}$, $R_{20}$, and $R_{21}$ are each independently selected from the group consisting of hydrogen, halo, $CF_3$, CN, $S(O)R_{22}$, $SO_2R_{22}$, $SO_2N(R_{22})_2$, $CON(R_{22})_2$, and straight or branched $C_{1-4}$ alkyl, or $R_{17}$ and $R_{18}$ may together form —CH=CH—CH'CH—, or $R_{18}$ and $R_{19}$ may together form —OCH$_2$O—; and $R_{22}$ is straight or branched $C_{1-3}$ alkyl, with the proviso that, when X is $(CH_2)_n$, then m and n are either both 0 or both 1.

18. The method of treatment of claim 17 wherein the disease state is treating cardiovascular diseases.

19. The method of claim 18 wherein the cardiovascular disease is selected from the group consisting of atrial and ventricular arrhythmias, Prinzmetal's (variant) angina, stable angina, exercise induced angina, congestive heart disease, and myocardial infarction.

20. The method of claim 17 wherein the therapeutically effective amount ranges from about 0.01 to about 100 mg/kg weight of the mammal.

21. The method of claim 17 wherein the mammal is a human.

22. The method of treatment of claim 17 wherein the disease state is protecting skeletal muscles against damage resulting from trauma.

23. The method of treatment of claim 17 wherein the disease state is protecting skeletal muscles subsequent to muscle or systemic diseases.

24. The method of treatment of claim 17 wherein the disease state is treating shock conditions.

25. The method of treatment of claim 17 wherein the disease state is preserving donor tissue and organs used in transplants.

* * * * *

UNITED STATES PATENT AND TRADEMARK OFFICE
CERTIFICATE OF CORRECTION

PATENT NO. : 6,677,343 B2
DATED : January 13, 2004
INVENTOR(S) : Blackburn et al.

It is certified that error appears in the above-identified patent and that said Letters Patent is hereby corrected as shown below:

Column 21,
Line 65, delete "$(CH_2)$" and replace -- $(CH_2)_n$ --.

Column 24,
Line 20, delete "-CH=CH-CH'CH-" and replace with -- -CH=CH-CH=CH- --

Signed and Sealed this

Sixth Day of July, 2004

JON W. DUDAS
*Acting Director of the United States Patent and Trademark Office*